United States Patent
Michelson

(10) Patent No.: US 7,297,147 B2
(45) Date of Patent: Nov. 20, 2007

(54) METHOD FOR CUTTING BONE OR CARTILAGE WITH A RONGEUR

(76) Inventor: Gary Karlin Michelson, 438 Sherman Canal, Venice, CA (US) 90291

( * ) Notice: Subject to any disclaimer, the term of this patent is extended or adjusted under 35 U.S.C. 154(b) by 44 days.

(21) Appl. No.: 11/371,387

(22) Filed: Mar. 9, 2006

(65) Prior Publication Data
US 2006/0149271 A1    Jul. 6, 2006

Related U.S. Application Data

(60) Division of application No. 10/765,341, filed on Jan. 27, 2004, now Pat. No. 7,011,663, which is a continuation of application No. 09/790,008, filed on Feb. 21, 2001, now Pat. No. 6,695,849, which is a continuation of application No. 08/108,908, filed on Aug. 18, 1993, now Pat. No. 6,200,320, which is a continuation-in-part of application No. 07/905,127, filed on Jun. 24, 1992, now abandoned, which is a continuation of application No. 07/398,987, filed on Aug. 28, 1989, now abandoned.

(51) Int. Cl.
 *A61B 17/32* (2006.01)
(52) U.S. Cl. .................................................. 606/83
(58) Field of Classification Search ............. 606/83, 606/170, 184; 600/567
See application file for complete search history.

(56) References Cited

U.S. PATENT DOCUMENTS

| | | | |
|---|---|---|---|
| 1,127,948 A | 2/1915 | Wappler | |
| 2,984,241 A | 5/1961 | Carlson | |
| 3,590,808 A * | 7/1971 | Muller | 600/565 |
| 3,628,524 A | 12/1971 | Jamshidi | |
| 3,752,161 A | 8/1973 | Bent | |
| 3,842,839 A | 10/1974 | Malis et al. | |
| 3,902,498 A | 9/1975 | Niederer | |
| 3,949,747 A | 4/1976 | Hevesy | |
| 4,122,856 A | 10/1978 | Mosior | |
| 4,201,213 A | 5/1980 | Townsend | |
| 4,416,278 A | 11/1983 | Miller | |
| 4,569,131 A | 2/1986 | Falk et al. | |
| 4,662,371 A | 5/1987 | Whipple et al. | |
| 4,722,338 A | 2/1988 | Wright | |
| 4,733,663 A | 3/1988 | Farley | |
| 4,760,848 A | 8/1988 | Hasson | |
| 4,777,948 A | 10/1988 | Wright | |
| 4,990,148 A | 2/1991 | Worrick, III et al. | |
| 5,009,661 A | 4/1991 | Michelson | |
| 5,026,375 A | 6/1991 | Linovitz et al. | |

(Continued)

FOREIGN PATENT DOCUMENTS

DE    85 18 482.9    10/1985

(Continued)

*Primary Examiner*—Michael Thaler
(74) *Attorney, Agent, or Firm*—Martin & Ferrero, LLP

(57) ABSTRACT

An improved multi-bite bone cutting rongeur with an ultrathin foot plate and a disposable cutting element and storage chamber unit is disclosed. The present invention has an integrated cutting element and storage chamber unit that is truly disposable, rather than merely replaceable. The present invention requires the use of no tools or special assembly. The chamber is simply placed onto the shaft whereby it is immediately locked into place by the use of the instrument.

20 Claims, 5 Drawing Sheets

U.S. PATENT DOCUMENTS

| | | |
|---|---|---|
| 5,061,269 A | 10/1991 | Muller |
| 5,273,519 A | 12/1993 | Koros et al. |
| 5,275,607 A | 1/1994 | Lo et al. |
| 5,385,570 A | 1/1995 | Chin et al. |
| 5,451,227 A | 9/1995 | Michaelson |
| 5,653,713 A | 8/1997 | Michelson |
| 5,702,420 A | 12/1997 | Sterling et al. |
| 5,782,849 A | 7/1998 | Miller |

FOREIGN PATENT DOCUMENTS

| | | |
|---|---|---|
| DE | 37 29 513 | 3/1988 |
| DE | 37 09 067 | 9/1988 |
| DE | 93 18 814 | 1/1994 |
| EP | 0 244 491 | 11/1987 |
| GB | 2 198 950 | 6/1988 |

* cited by examiner

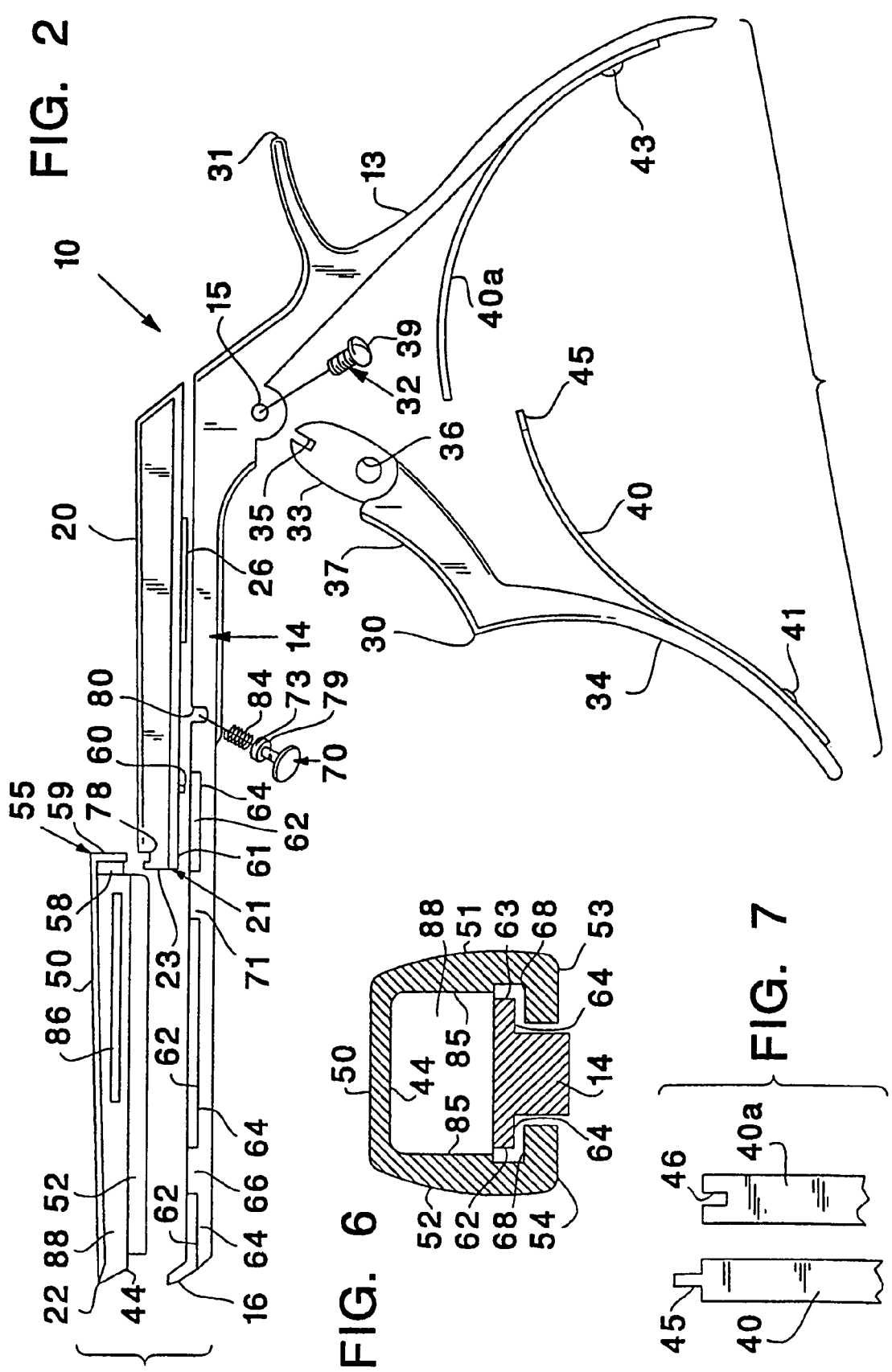

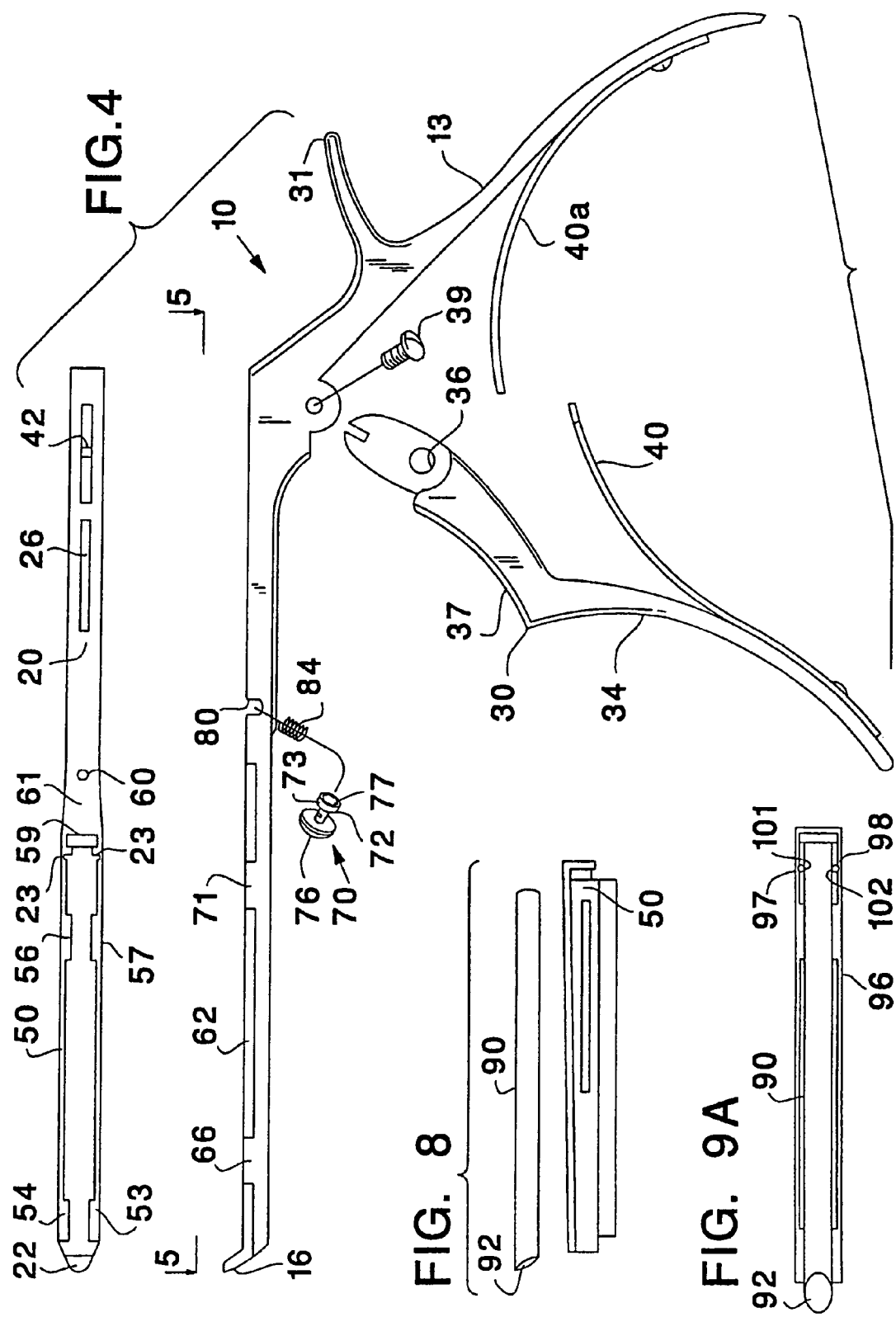

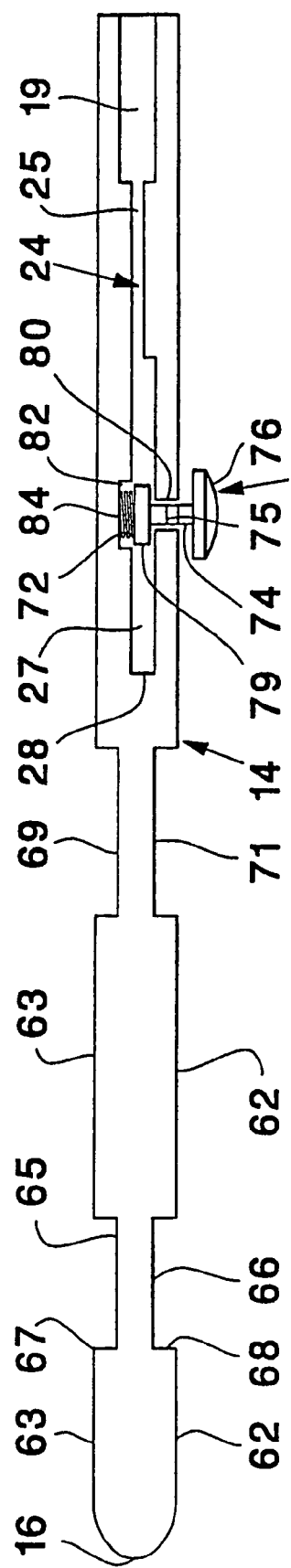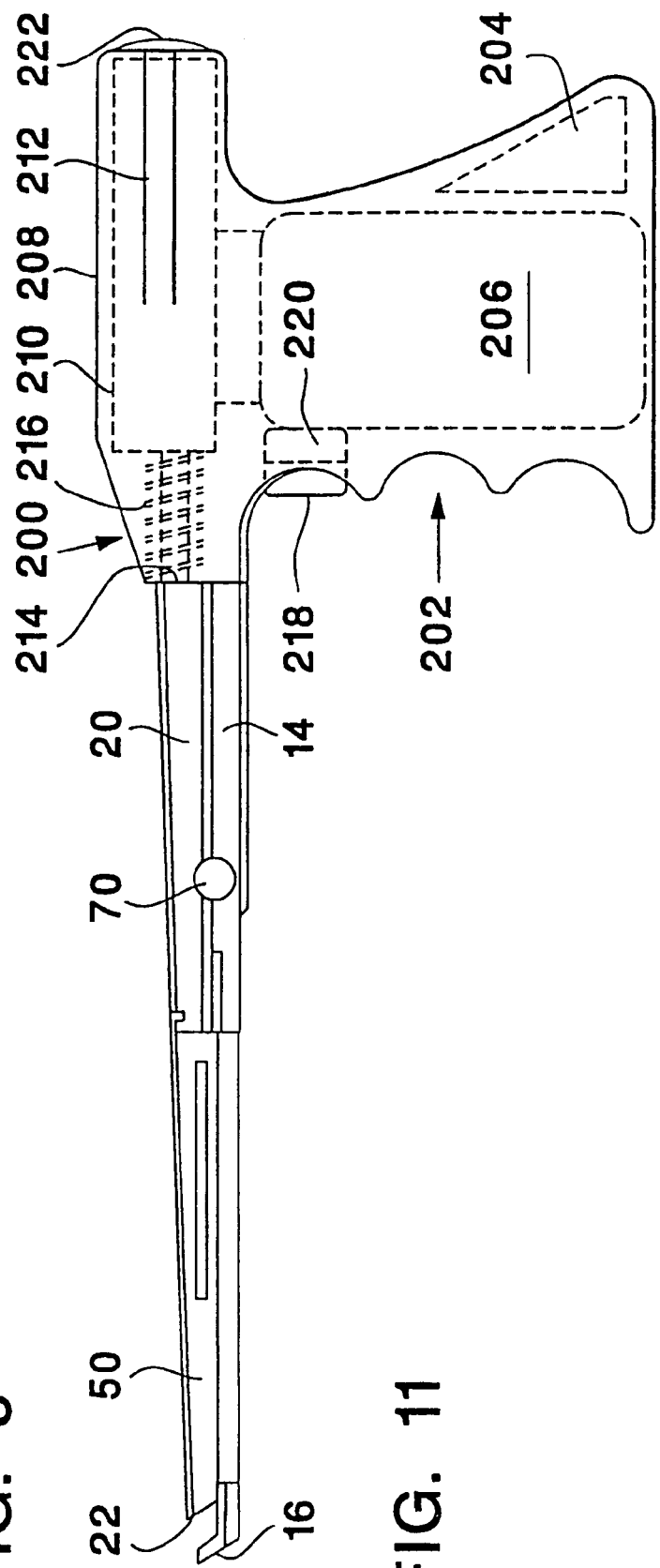
FIG. 5
FIG. 11

METHOD FOR CUTTING BONE OR CARTILAGE WITH A RONGEUR

This application is a divisional of application Ser. No. 10/765,341, filed Jan. 27, 2004 now U.S. Pat. No. 7,011,663; which is a continuation of application Ser. No. 09/790,008, filed Feb. 21, 2001, now U.S. Pat. No. 6,695,849; which is a continuation of application Ser. No. 08/108,908, filed Aug. 18, 1993, now U.S. Pat. No. 6,200,320; which is a continuation-in-part of application Ser. No. 07/905,127, filed Jun. 24, 1992, now abandoned; which is a continuation of application Ser. No. 07/398,987, filed Aug. 28, 1989, now abandoned; all of which are incorporated herein by reference.

BACKGROUND OF THE INVENTION

1. Field of the Invention

This invention relates to surgical instruments, and more particularly to surgical instruments used to bite out or cut portions of bone or cartilage.

2. Description of the Related Art

Rongeurs are surgical instruments for the cutting away of human tissue, and most commonly, cartilage and/or bone. At present there is a need for a rongeur having a less cumbersome and less intrusive foot plate which would make the instrument safer for use in the spinal canal and about the delicate neural structures and extend the range of use of the instrument by allowing it to be used in closer proximity to those same structures.

Attempts have been made in the past to provide a rongeur with a less cumbersome foot plate. For example, U.S. Pat. No. 4,990,148 issued to Worrick, III. et al. ("Worrick") on Feb. 5, 1991 teaches a means for allowing a limited reduction of the foot plate thickness by the addition of a groove placed at the junction of the foot plate to the shaft for the purpose of relieving crossed fields of stress. However, the foot plate of Worrick is still internally cupped to maintain a cutting edge, which thus limits any further reduction in the thickness of the foot plate.

Essentially flat foot plates had been in use earlier this century, but proved to be undesirable because spinal bone is markedly compressed during the biting process. When the foot plate is flat, the mass of bone bitten is forcefully compacted into the singularly cupped recess of the movable jaw such that it is extremely difficult to remove that bone after each bite.

At present, there is also a need for a rongeur with a capacity to remain within the wound and to repeatedly bite and to store the bone bitten until all the requisite bone removal has been completed without the need to continuously remove the rongeur from the wound for the purpose of removing the bone from the instrument to clear the cutting edges. A further and related need is for a rongeur that would collect and contain all of the bitten material such that the delicate neural structures would be protected from contact with the bitten material and/or any cogenerated inadvertent debris. In this regard, any rongeur can bite more than once, but not properly. That is, one could deliberately take several small bites, each of which would fail to fill the cup in the foot plate and the singularly cupped recess of the moveable jaw, in lieu of taking one full bite. However, once the cup and the cupped recess are filled further biting is not possible. Bone may be crushed as cups that are already full approach one another, but their contents will shield any further interposed bone from the cutting edges, thus making any further bone cutting impossible.

An example of a multibite rongeur is shown in U.S. Pat. No. 3,902,498 issued to Niederer on Sep. 2, 1975. Niederer teaches the use of a rongeur hollow at the tip such that it is possible to take several bites. Unfortunately, since the hollow tip is open to the wound at both ends, the further use of the instrument pushes the already bitten material out of the other end of the hollow tip and back into the depths of the surgical wound where it can cause great harm.

Finally, there is also a need for a surgical rongeur that will upon each use present a perfectly formed and razor sharp cutting edge, which will mate exactly, and close completely, to the opposed foot plate. In this regard, Niederer taught the use of a disposable cutting element but not the use of a disposable storage chamber for the cut pieces.

Of note is U.S. Pat. No. 5,026,375 issued to Linovitz et al. on Jun. 25, 1991 which claims a modification of Niederer's teaching wherein the tip is replaceable rather than disposable, in that it requires assembly and is secured with a screw, and wherein the tip has extending from its lower surface an inverted "T" shaped portion made to be inserted into and engage with a correspondingly internally disposed inverted "T" slot within a portion of the instrument shaft.

A further problem with the design of conventional rongeurs limiting further thinning of the foot plate so as to maintain adequate strength is that since the opening of a conventional rongeur is much greater in its capacity than the sum volume of its cuts, in the process of biting with such a rongeur, the bone is not only bitten but is further compacted under tremendous pressure, that pressure being transmitted directly to the foot plate.

Conventional rongeurs by design have excursions beyond that needed to merely close the jaw completely when the rongeur is new. That is because the manufacturer must allow for the wear that will occur at the cutting edges, and yet still provide for the capacity of the instrument to still close fully later. Thus, when bone is bitten with a conventional rongeur, a force considerably greater than that necessary to cut or even compact the bone is additionally transmitted to the foot plate as the slidable member attempts further proximal migration in opposition to the foot plate.

SUMMARY OF THE INVENTION

The present invention is an ultra-thin foot plate, multi-bite rongeur with an integral storage chamber and cutting element that is replaceable and disposable. The integral storage chamber and cutting element of the present invention is removably locked to a central shaft and is removably engaged to a driving member. The integral storage chamber and cutting element slides along the shaft towards a foot plate at the distal end of the shaft in response to the movement of the driving member which may be hand operated or powered by a solenoid or a pneumatic means.

The ultra-thin foot plate of the present invention is made possible by the complete absence of a cup. The foot plate shaft junction area of the present invention is designed to mitigate the stress concentration of the junction. The foot plate of the present invention need not be as thick as that of a conventional rongeur since the only force applied to it is that sufficient to actually cut the bone being bitten. During use, the integral storage chamber and cutting element is closed at its proximal end and open at its distal end terminating in an ultra-sharp cutting surface. The interior cross sectional area of the storage chamber flares in both height and width from distal to proximal. Inasmuch as the cutting element storage chamber unit is hollow, rather than cupped, and the opposed surface of the foot plate is flat, the bone bitten is always driven rearward into the chamber portion. As the storage chamber is closed while in use except for the cutting entrance, it may be used to repeatedly bite bone without the danger of the bone bitten coming free and falling into the spinal canal.

When the present invention has completed its task and removed all of the bone as needed, the integral storage chamber and cutting element may be removed from the shaft of the rongeur and the bitten bone may be removed from the storage chamber and made available for use, as in performing a spinal fusion.

The present invention allows for the clean cutting of bone or cartilage without any compaction. Further, as the cutting element of the present invention is disposable and thus always fresh and sharp, less force is required during the actual cutting of the bone. In addition, since the integrated cutting element storage chamber unit is always fresh and sharp, edge wear is not a problem and the capacity for further excursion of the cutting element towards the foot plate is unnecessary and may be completely blocked, thereby sparing damage to the foot plate.

Finally, the present invention has an integrated cutting element and storage chamber unit that is truly disposable, rather than merely replaceable and requires no special assembly or the use of any tools. The integrated cutting element and storage chamber is simply placed onto the shaft whereby it is immediately locked into place by the use of the instrument itself.

OBJECTS OF THE PRESENT INVENTION

It is an object of the present invention to provide an improved surgical rongeur capable of making multiple bites or cuts of bone or cartilage without being removed from the wound after each bite or cut.

It is another object of the present invention to provide an improved surgical rongeur capable of storing multiple cut pieces of bone or cartilage while the rongeur is in the wound.

It is yet another object of the present invention to provide an improved surgical rongeur having an integrated cutting element and storage chamber.

It is a further object of the present invention to provide an improved surgical rongeur having an integrated cutting element and storage chamber unit that is easily replaceable and disposable.

It is yet a further object of the present invention to provide an improved surgical rongeur having a replaceable and disposable integrated cutting element and storage chamber unit that does not require the use of tools or special assembly.

It is still a further object of the present invention to provide an improved surgical rongeur having an integrated cutting element and storage chamber unit where the integrated cutting element and storage chamber is simply placed onto the shaft whereby it is immediately locked into place by the use of the instrument.

It is another object of the present invention to provide an improved surgical rongeur with an ultra-thin foot plate that is flat.

It is yet another object of the present invention to provide an improved surgical rongeur that allows for the clean cutting of bone or cartilage without any complication.

These and other objects of the present invention shall be more clear upon review of the following detailed description of the drawings when reviewed in conjunction with the accompanying drawings.

BRIEF DESCRIPTION OF THE DRAWINGS

FIG. 2 is an exploded first side view of an improved bone rongeur constructed in accordance with the present invention.

FIG. 4 is a bottom plan view of the slide drive member engaged to the cutting/storage member and a side view of the body of the surgical rongeur of the present invention.

FIG. 5 is a top plan view along lines 5-5 of FIG. 4 of the shaft portion of the rongeur of the present invention showing the configuration of the slot and recess.

FIG. 6 is a cross sectional view along lines 6-6 of FIG. 1.

FIG. 7 is a partial schematic view of the spring means for biasing the handle of the rongeur of the present invention.

FIG. 8 is a perspective view of an alternative embodiment of the cutting/storage member of the present invention including a disposable storage and cutting element.

FIGS. 9A and 9B are perspective views of further alternative embodiments of the cutting/storage member of the present invention including a disposable storage and cutting element secured to the bottom portion of a carrier member.

FIG. 11 is a perspective side view of an alternative embodiment of the present invention showing a power rongeur.

DETAILED DESCRIPTION OF THE DRAWINGS

Figure 1:
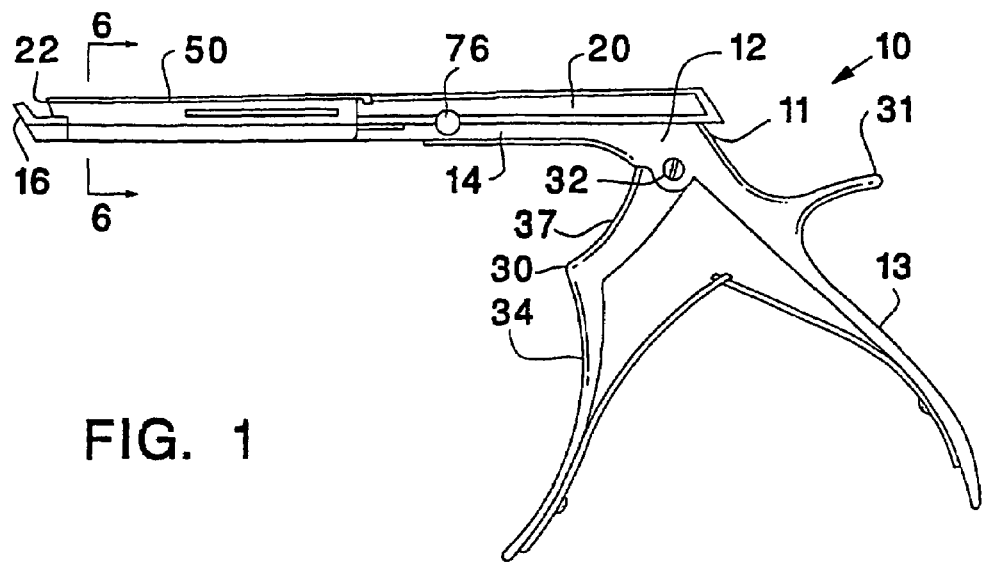
FIG. 1 is a perspective side view of an improved bone rongeur constructed in accordance with the present invention.
Figure 3:
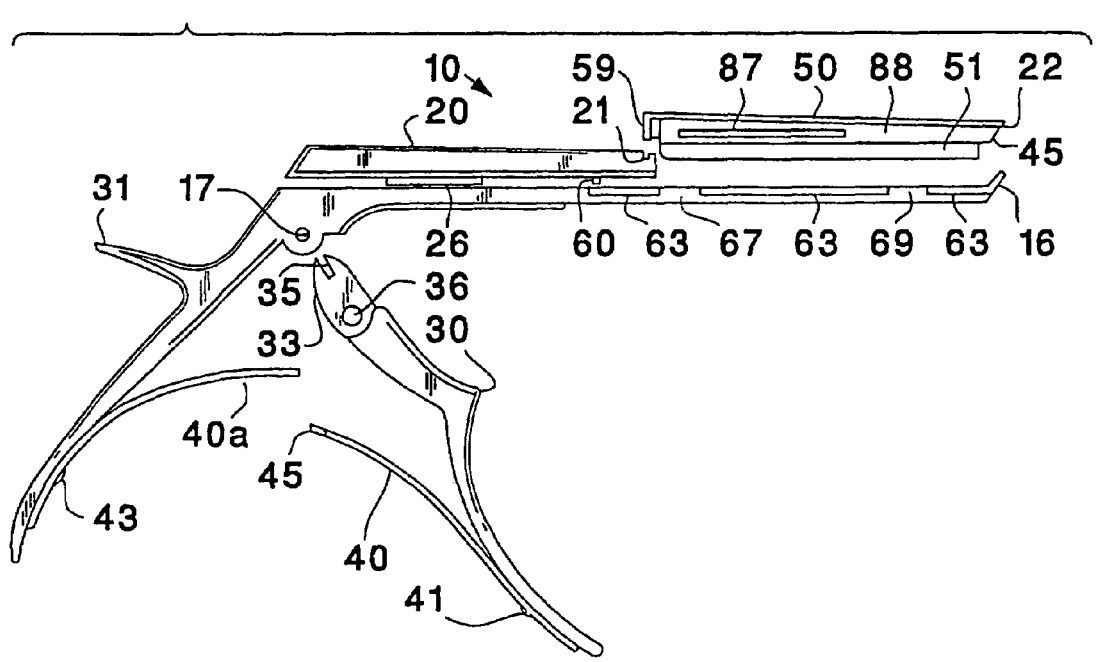
FIG. 3 is an exploded second side view of an improved bone rongeur constructed in accordance with the present invention.

Referring to FIGS. 1-4, the improved surgical bone rongeur 10 is shown constructed in accordance with the present invention and consists generally of a body 12 having a rear handle 13 depending at an angle from the proximal end 11 of the body 12, and has a shaft 14 extending distally and terminating at its distal end in a foot plate 16. A support spike 31 extends from the upper portion of the rear handle 13 as support for the area of the hand between the thumb and the first finger. Mounted on the shaft 14 is a slide drive member 20 for reciprocating movement on the shaft 14. The slide drive member 20 has a pin 42 located at its bottom surface near its proximal end as shown in FIG. 4.

Referring to FIG. 2, a pivoting forward handle 30 includes a lower finger grip portion 34 and an upper finger portion 37 for the fingers. The upper part of the forward handle 30 has an extension 33 with an elongated opening 35 and an aperture 36 through which passes a pivot pin 32. Extension 33 fits into the body 12 through slot 19 (shown in FIG. 5) and is contained within the body 12.

Once the extension 33 is positioned within slot 19, the pivot pin 32, having a screw head 39 on one end and threads at its other end, is used to pivotally attach the forward handle 30 to the body 12. The pivot pin 32 passes through opening 15 in one side of the body 12 through aperture 36 in the forward handle 30 and threads into threaded aperture 17 in the other side of the body 12. The elongated opening 35 of the extension 33 surrounds the pin 42 of slide drive member 20 mounted on the shaft 14 so that the forward handle 30 engages the pin 42 and serves as the driving means for the slide drive member 20. The forward handle 30 is attached to the body 12 at an angle to the slide drive member 20 so that when the forward handle 30 moves proximally the slide drive member 20 moves distally.

The forward handle 30 and the rear handle 13 are biased away from each other by spring means 40 and 40a. Spring means 40 is attached at one end to the bottom of forward handle 30 by screw 41 and spring means 40a has one end attached to the bottom of rear handle 13 by screw 43. In order to interlock the two spring means 40 and 40a, spring means 40 has an extension piece 45 at its upper end that fits into the notch 46 of the upper end of spring means 40a as shown in FIG. 7. Once interlocked, the spring means 40 and 40a oppose each other to bias the forward handle 30 distally. Other spring mechanisms, internal or external, and other biasing means, including pneumatic means, may also be employed for urging the forward handle 30 distally.

Referring to FIGS. 4 and 5, the slide drive member 20 is slidably mounted to the top surface of shaft 14 within a slot 24 formed in the shaft 14 having an inverted T-shaped portion 25 into which is fitted a complementary inverted T-shaped runner 26 depending from the bottom surface of slide drive member 20. Slot 24 extends distally from the inverted T-shaped portion 25 to form a wider portion 27 of the slot 24.

Referring to FIG. 4, a stop pin 60 depends from the distal end 61 of the bottom surface of the slide drive member 20. The stop pin 60 serves to guide the slide drive member 20 to keep the distal end 61 of the slide drive member 20 from sliding off the shaft 14 during the operation of the rongeur 10. The stop pin 60 is set back from the distal end 61 of the slide drive member 20 and fits within the wider portion 27 of slot 24. The wider portion 27 of the slot 24 has a slot wall 28 at its distal end which catches the stop pin 60 and prevents the slide drive member 20 from sliding off the shaft 14 distally.

Referring back to FIG. 2, on one side of the shaft 14 is a rounded aperture 80. The rounded aperture 80 corresponds in location to a recess 82 in the top surface of shaft 14 as shown in FIG. 5. The recess 82 bisects the wider portion 27 of slot 24 and has a rounded bottom surface. Located within the recess 82 and extending from the aperture 80 is a push button assembly 70 having a large diameter, external button portion 76 and a narrow diameter portion 74 that passes through the aperture 80. The narrow diameter portion 74 has a depression 75 with a flat bottom. The narrow diameter portion 74 terminates at its other end in a large diameter member 72 having a slightly smaller diameter than the diameter of the rounded recess 82. The large diameter member 72 has a flattened top surface 73 so that it is flush with the top surface of the shaft 14 when the large diameter member 72 is inserted within the recess 82. The reverse end of the large diameter member 72 has a small depression 77 for receiving the end of a coil spring 84 a shown in FIG. 4.

The large diameter member 72 is placed within the recess 82, so that the narrow diameter portion 74 crosses the wider portion 27 of the slot 24 at a right angle and extends through the rounded aperture 80 and the external button portion 76 is external to the shaft 14. The depression 75 in the narrow diameter portion 74 is of a sufficient depth to permit the stop pin 60 depending from the slide drive member 20 to easily pass through the wider portion 27 of the slot 24 and over the depression 75 unobstructed by the narrow diameter portion 74.

Within the recess 82 is a coil spring 84 having an end that fits within the small depression 77 of the large diameter member 72. The coil spring 84 serves to bias the large diameter member 72 so that in its biased position, the large diameter member 72 blocks the wider portion 27 of slot 24.

The large diameter member 72 has a diameter that is sufficient to prevent the stop pin 60 from sliding over it. The external button portion 76 is at its greatest extension out of the rounded opening 80 when the large diameter member 72 is in the biased position and blocks the wider portion 27 of the slot 24. To unblock the wider portion 27 of the slot 24, the user simply presses the external button portion 76 of the button assembly 70 so that the coil spring 84 compresses and the large diameter member 72 moves further into the recess 82. When the large diameter member 72 is positioned as far into the recess 82 as possible the depression 75 of the button assembly 70 is positioned directly beneath the stop pin 60 depending from the bottom surface of the slide drive member 20 so that the stop pin 60 can pass through the wider portion 27 of the slot 24 unobstructed.

It is appreciated that the rounded recess 82 may be placed at various locations along the shaft 14 so that the button assembly 70 contained therein may also be positioned at various locations along the shaft 14 beneath the slide drive member 20. The position of the stop pin 60 depending from the slide drive member 20 may also be changed to correspond to the location of the button assembly 70 and the configuration of the slot 24 and the position of the wider portion 27 may also be modified accordingly without departing from the scope of the present invention. For example, the rounded recess 82 may be positioned along the shaft 14 so that it is located above the opening 15 and the threaded aperture 17 of the body 12. In this position, the button assembly 70 in addition to controlling the displacement of the slide drive member 20 along the shaft 14 could also serve as a hinge and attachment means for the forward handle 30 replacing the pivot pin 39.

As shown in FIG. 5, the shaft 14 has a pair of rails 62,63 extending from either side of the shaft 14 which run parallel to the shaft 14. The rails 62,63 have a bottom flat surface 64 that is perpendicular to the sides of the shaft 14 as shown in FIG. 6. Near the distal end of the shaft 14 are forward notches 65,66 that provide a break in the continuity of the rails 62,63. Positioned proximal to the forward notches 65,66 are rear notches 69,71 which similarly provide a break in the continuity of the rails 62,63.

The distal end 61 of the slide drive member 20 engages a cutting/storage member 50 which is removably attached to both the shaft 14 and to the slide drive member 20. The cutting/storage member 50 has depending sides 51 and 52 which are mirror images of each other. As shown in FIG. 4, near the distal end of the cutting/storage member 50 the depending sides 51,52 each have forward rail-engaging members 53,54 respectively. Forward rail-engaging members 53,54 fit within the forward notches 65,66 of shaft 14. Each of the forward rail-engaging members 53,54 has a top flat surface 68 that is perpendicular to the depending sides 51 and 52 for engaging the bottom flat surface 64 of rails 62,63 as shown in. FIG. 6. Once the forward rail-engaging members 53,54 are engaged to the rails 62,63, the cutting/storage member 50 is prevented from sliding upward as it moves along the shaft 14.

Also located on each of the depending sides 51,52 of the cutting/storage member 50 are rear rail-engaging members 56,57 which are sufficiently spaced proximally from the forward rail-engaging members 53,54 so that when the forward rail-engaging members 53,54 are placed over forward notches 65,66, the rear rail-engaging members 56,57 are directly over the rear notches 69,71 in the shaft 14. The rear rail-engaging members 56,57 are identical to the forward rail engaging members 53,54 and similarly each have a top flat surface 68 for engaging the bottom flat surface 64 of rails 62,63.

Referring to FIGS. 2 and 4, the proximal end of the cutting/storage member 50 has a male connection means 55 having grooves 58 on both sides of a key portion 59. The male connection means 55 fits into a female connection means 21 located at the distal end 61 of the slide drive member 20. The female connection means 21 has rails 23 for engaging the grooves 58 of the male connection means 55 and a notched area 78 for receiving the key portion 59. The cutting/storage member 50 may be engaged to the slide drive member 20 by lowering the cutting/storage member 50 toward the slide drive member 20 so that the male and female connection means 55 and 21 slide into each other. To disengage the cutting/storage member 50 from the slide drive member 20, the cutting storage member 50 is simply lifted out. As an alternative, the cutting/storage member 50 may also be attached to the slide drive member 20 in any number of conventional ways, such as by snap fit.

The cutting/storage member 50 is placed on the shaft 14 by aligning the forward rail-engaging members 53,54 with the forward notches 65,66 and by simultaneously aligning the rear rail-engaging members 56,57 with the rear notches 69,71 so that the male connection means 55 slides into and engages the female connection means 21 of the slide drive member 20. In order to properly align the cutting/storage member 50 so that it may engage the shaft 14, the slide drive member 20 must be positioned sufficiently proximal from the foot plate 16.

The range of proximal to distal movement of the slide drive member 20 is controlled by the large diameter member 72 of the button assembly 70. In its biased position, the large diameter member 72 is positioned in the wide portion 27 of slot 24 so that the distal edge 79 of the large diameter member 72 blocks the stop pin 60 and thus the slide drive member 20 from moving proximally along shaft 14. The appropriate position of the slide drive member 20 for attaching the cutting/storage member 50 to the shaft 14 may only be achieved by sliding the stop pin 60 past the position of the distal edge 79 of the large diameter member 72. In order to slide the stop pin 60 past the distal edge 79, the button assembly 70 must be manually depressed toward the shaft 14 so that the large diameter member 72 is pushed into the recess 82 and is moved out of the wide portion 27 of slot 24. As the forward handle 30 is biased forward by the spring means 40 and 40a, the slide drive member 20 is moved proximately along the shaft 14 so that the stop pin 60 is positioned within the depression 75 of the narrow diameter portion 74. With the stop pin 60 positioned within the depression 75, the large diameter member 72 is pushed back within the recess and the coil spring 84 is compressed within the recess 82 of the shaft 14.

Once aligned with the forward and rear notches 65,66 and 69,71 and engaged to the slide drive member 20, the cutting/storage member 50 is in position to be pushed distally along shaft 14 by the slide drive member 20 toward the foot plate 16. This is accomplished by squeezing the forward handle 30 to move the slide drive member 20 and the stop pin 60 distally so that the stop pin 60 is no longer within the depression 75 of the narrow diameter portion 74, and the large diameter member 72 is returned to its biased position by the coil spring 84. As the cutting/storage member 50 is engaged to the slide drive member 20, the movement of the cutting/storage member 50 is responsive to the movement of the slide drive member 20. As the cutting storage member 50 is moved distally the front and rear rail-engaging members 53,54 and 56,57 engage the rails 62,63.

Once the cutting/storage member 50 engages the rails 62,63 of the shaft 14, it may not be lifted out and the cutting/storage member 50 is locked to the shaft 14. The proximal movement of the slide drive member 20 is stopped by the large diameter member 72 in its biased position which blocks the stop pin 60 from further proximal travel in the wider portion 27 of the slot 24. To remove the cutting/storage member 50 from the shaft 14, the stop pin 60 must be again positioned by the user so that it is within the depression 75 of the narrow diameter portion 74. Thus, the cutting/storage member 50 may be locked or unlocked to the shaft 14 without the use of tools by simply pressing the button assembly 70.

The distal end of the cutting/storage member 50 opens into a storage chamber 88 which is bounded by upper and side walls 44 and 85 which are sharpened to form cutting edges 22 facing the foot plate 16. The depending sides 51,52 of cutting/storage member 50 are recessed from the foot plate 16 for maximum bite since no cutting edge is required at the depending sides 51,52. While the foot plate 16 may have a slight concave depression, it is to be understood that it is preferable substantially flat, with or without a cutting edge.

The storage chamber 88 extends along the interior of the cutting/storage member 50-at least partially toward its proximal end. The cross sectional area of the interior of the storage chamber 88 may be constant or preferably progressively increases from the distal end to the proximal end so that a number of successive bone fragments can more easily slide into the storage chamber 88 and stack up without jamming.

The rongeur 10 of the present invention is used in the conventional manner to bite bone or cartilage. The cut bone fragments are pushed by the foot plate 16, one by one, into a stack within the storage chamber 88 of the removable cutting/storage member 50 after being cut and are not likely to fall back into the wound site because they are forced into the storage chamber 88 with considerable force and are prevented from jamming as the cross sectional area of the interior space of the storage chamber 88 increases from distal to proximal away from the cutting edge 22. Thus, it is not necessary that the cut bone fragments be removed during the surgical procedure, and bite after bite takes place, without the need to remove the rongeur 10 from the wound.

In the preferred embodiment, the side walls 44 and 85 of the cutting/storage member 50 have narrow slits 86,87 partially along the length of the cutting/storage member 50. Once the cutting/storage member 50 is filled with cut pieces of bone, it is removed from the shaft 14 and a stylet or similar instrument may be inserted through the slits 86,87 on either of the side walls 44,85 to aid in the removal of the cut pieces from the storage chamber 88 containing the cut pieces.

Alternatively, the proximal end of the storage chamber 88 of the cutting/storage element 50 may also be open. During use, the distal end 61 of the slide drive member 20 may be used to block the open proximal end of the storage chamber 88. Once the cutting/storage element 50 is removed from the rongeur 10, the proximal end of the storage chamber 88 is open and a stylet may be used to push the cut bone fragments stored within the storage chamber 88 so that the fragments exit from the distal end.

The use of a removable hollow cutting/storage member 50 permits a new sharp cutting edge to be provided for each operation as it may easily be replaced. Both the storage chamber 88 and the cutting edge 22 could be made of metal or any other suitable material such as ceramic for the edge or a plastic (e.g. polycarbonate) for the storage chamber 88.

In the preferred embodiment, the rongeur 10 has a body 12 that is approximately 7¼ inches in length; a cutting/storage member 50 that is approximately 3¼ inches in length and approximately ⅞ inches in height and approximately ⅜ inches in width; a slide drive member 20 that is approximately 3 9/16 inches in length and approximately ⅞ inches in height and approximately ⅜ inches in width; a rear handle 13 approximately 4⅞ inches in length and a front handle 30 approximately 4⅜ inches in length having a extension member 33 that is approximately ⅞ inches long; and a button assembly 70 having an overall length of approximately 7/16 inches.

In an alternative embodiment of the present invention, the rongeur 10 includes a removable and disposable straw 90 as part of the cutting/storage member 50 as shown in FIG. 8. Straw 90 is a hollow member in the shape of a cylinder or may have any other shape suitable for use with rongeur 10. At the distal end of the straw 90 is a sharp cutting edge 92 for cutting bone or other similar tissue. The straw 90 has a diameter that is sufficiently sized so that it may be inserted within the storage chamber 88 of the cutting/storage member 50. In this embodiment, the distal end of the cutting/storage member 50 is truncated so that the cutting edge 92 at the distal end of straw 90 extends from the chamber 88 and may be used to cut bone or cartilage against the foot plate 16. In this embodiment, the cutting/storage member 50 is actually a carrier member as the straw 90 does the actual cutting and storing of the bone. Prior to use, the straw 90 is inserted within the storage chamber 88 before the cutting/storage member 50 is placed on the shaft 14. The hollow chamber 94 of the straw 90 functions to store the cut pieces of bone or cartilage. The stored cut pieces may be removed for future use in the same manner described above for the preferred embodiment.

Straw 90 has an open distal end and a proximal end that may be closed during use of the rongeur. Additionally, straw 90 may have a cross sectional area that increases from its distal end to its proximal end.

Figure 9B:
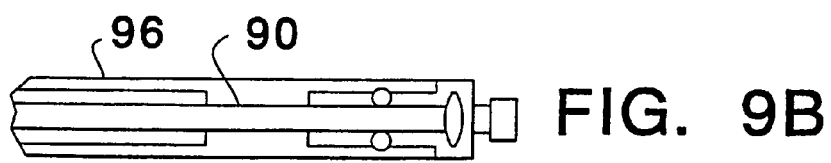

In a further alternative embodiment, the straw 90 instead of being inserted within the storage chamber 88 is affixed to the bottom of a modified cutting/storage base 96 as shown in FIGS. 9A and 9B. The cutting/storage base 96 is identical in construction to the cutting/storage member 50 but does not have the storage chamber 88 and essentially acts as a housing for carrying the straw 90. The straw 90 is placed in the bottom of the cutting/storage base 96 prior to placing the cutting/storage base 96 on the shaft 14. The straw 90 is held in place and is prevented from rotating by pins 97,98 which complement the grooves 101,102 in the straw 90 as shown in FIG. 9A, and prevent any movement of the straw 90 within the cutting/storage base 96 during the operation of the rongeur. Once the cutting/storage base 96 is removed from the shaft 14, the straw 90 is easily removable from the cutting/storage base 96.

The straw 90 is preferably made of metal or any other material which is capable of being sharpened and maintaining a sharp cutting edge 92 for multiple bites by the rongeur 10. After the straw 90 is used and removed from the rongeur 10, the cut pieces contained therein are removed and may be used for bone grafting purposes if desired. The relatively low cost of the straw 90 allows the straw 90 to be truly disposable.

Figure 10A:
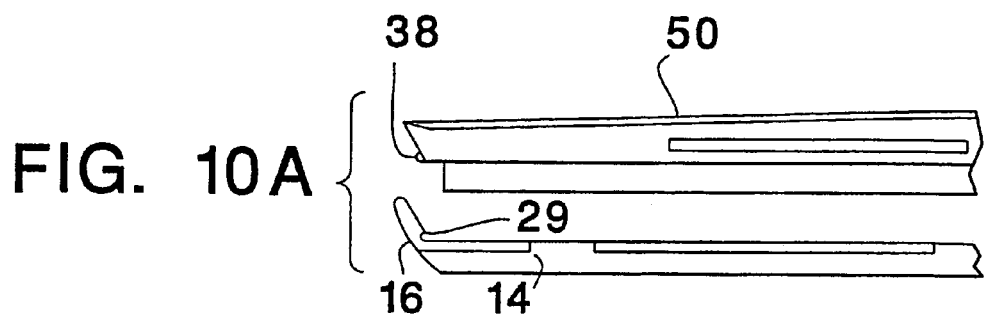
FIGS. 10A and 10B show a partial schematic side view of another alternative embodiments of the foot plate and the cutting/storage member of the present invention.
Figure 10B:
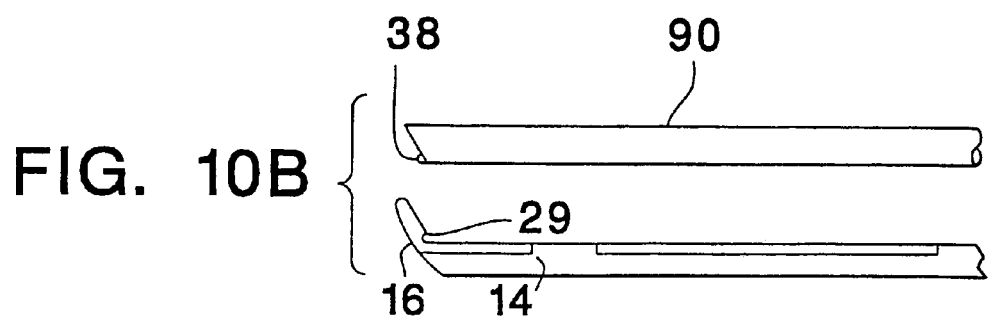

As a further alternative embodiment of the rongeur 10, the intersection of the foot plate 16 and the shaft 14 may have a groove 29 as shown in FIGS. 10A and 10B to relieve crossed fields of stress. In this embodiment, the distal end of the cutting/storage member 50 or of a straw 90 has an extension element 38 that complements the shape of the groove 29 and fits within the groove 29. The extension element 38 may be made of the same material as the cutting/storage member 50 or the straw 90 or may be a flexible material such as plastic. As a result of the angled orientation of the foot plate 16, when the rongeur is fully closed, the cutting/storage member 50 or the straw 90 tends to be forced up the inclination of the foot plate 16 which may result in damage to the cutting edge 22 or 92. The combination of the groove 29 and the extension element 38 functions to prevent any further upward excursion of the cutting/storage member 50 or straw 90 and thus prevents additional force from being applied to the foot plate 16 and prevents any possible damage to the cutting surfaces of the rongeur 10.

The operation of the rongeur 10 of the present invention is as follows:

The rongeur 10 is set in the "release position" by positioning the stop pin 60 within the depression 75 of the narrow diameter portion 74 of the button assembly 70. This is accomplished by manually pressing the external button portion 76 of the button assembly 70 so that the large diameter member 72 moves out of the wider portion 27 of the slot 24 to compress the coil spring 84. The stop pin 60 may now freely pass by the position of the distal edge 79 of the large diameter member 72 and to fit within the depression 75. As the spring means 40 and 40a bias the forward handle 30 distally, the slide drive member 20 moves toward the foot plate 16. With the stop pin 60 positioned within the depression 75, the coil spring 84 is kept compressed within the recess 82.

In the release position, the slide drive member 20 is positioned so that the cutting/storage member 50 may be easily placed on the shaft 14. In the release position, the forward rail-engaging members 53,54 are aligned with the forward notches 65,66 and the rear rail-engaging members 56,57 are aligned with the rear notches 69,71. Once aligned, the cutting/storage member 50 is positioned to easily engage the slide drive member 20 so that the male and female connector means 55 and 21 mate and the cutting/storage member 50 rests upon the shaft 14.

Once the cutting/storage member 50 is engaged to the slide drive member 20, the forward handle 30 is squeezed by the user to advance the slide drive member 20 so that the stop pin 60 exits from within the depression 75 and the large diameter member 72 is returned by the coil spring 84 to its biased position to block the wider portion 27 of the slot 24. With the large diameter member 72 in this position, the stop pin 60 is stopped from any further proximal movement past the distal edge 79 of the large diameter member 72 thereby preventing any further proximal movement of the slide drive member 20 past the large diameter member 72. With the slide drive member 20 in this position, the forward and rear rail engaging members 53,54 and 56,57 are engaged to the rails 62,63 and are no longer aligned with the forward and rear notches 65,66 and 69,71. Therefore, the cutting/storage member 50 is securely locked to the shaft 14 and may not be removed from the shaft 14.

With the cutting/storage member 20 in the locked position on the shaft 14, the rongeur 10 may be placed in the wound and used to take multiple bites or cuts of the selected tissue with the cut pieces being stored within the storage chamber 88 of the cutting/storage element 50. Once the desired number of bites has been attained or if the storage chamber 88 becomes filled, the rongeur 10 is removed from the wound. The cutting/storage member 50 is removed from the shaft 14 of the rongeur by returning the rongeur to the release position by pressing the external button portion 76 as described above, so that the forward and rear rail-engaging members 52,54 and 56,57 are once again aligned with the forward and rear notches 65,66 and 69,71 and no longer engage the rails 62,63. The cutting/storage member 50 is then easily lifted up and away from the shaft 14.

The cut pieces may be removed from the storage chamber 88 by inserting a stylet in the slits 86,87 in the side walls 44,45 of the cutting/storage member 50 and pushing the cut pieces out from the chamber. If an alternative embodiment of the cutting/storage element 50 is used where the proximal end of the storage chamber 88 is closed only during use, the cut pieces may be pushed out of either end of the storage chamber 88. Similarly, if a disposable straw 90 is used, the cut pieces contained within the straw 90 may be removed by using a stylet to the push the cut pieces out of either the proximal or the distal end of the straw 90 which are both open when not in use.

While the preferred embodiment of the present invention is a hand powered instrument, the use of alternative power sources such as electricity, battery supply, pneumatic, or other power sources can be employed.

In a powered rongeur, the finger grip of the rongeur can then be devoted to turning on and off the power supply source to drive the instrument. If gas or other fluid is used, a pressure relief valve is preferably incorporated within the fluid line to establish a limit pressure, which may be set to the maximum desired biting force to be delivered.

Referring to FIG. 11, a powered rongeur 200 is shown. The grip 202 is adapted for receipt of the electronic circuitry 204 and the rechargeable battery pack 206. A cover (not shown) holds the battery pack 206 within the grip 202.

Above the grip 202, is a housing 208 containing a wire coil 210 that surrounds a reciprocating rod 212. The rod 212 is connected at one end 214 to the slide drive member 20. The rod 212 is spring biased by a strong spring 216 in the proximal direction. Whereby, upon activation of the trigger 218 which closes switch 220, the rod 212 is driven forward driving the slide drive member 20 and the cutting/storage member 50 toward the foot plate 16. The speed of the rod 212 would result in additional cutting force, due to the momentum of the slide drive member 20. As a safety precaution, the momentum at which the rod 212 is driven forward may be set to a desired rate so that excessive force is not exerted on the cutting edge 22 and the foot plate 16. For example, the momentum generated by the coil 210 and the rod 212 may be set at a desired rate for cutting bone or cartilage so that the rongeur 200 will not bite a hard object, such as a metal pin, which requires a greater momentum to cut and would damage the foot plate 16 and the cutting edge 22.

Pulling of the trigger 218 closes the switch 220 to cause one closing and opening of the rongeur 200. For a second closing operation, the trigger 218 must be released and then depressed again in order to close switch 220 once again.

The rear portion of the housing 208 can be opened for access to the compartment by the removal of cap 222. Prior to sterilization, the cap 222 and the coil 210 can be removed from the housing 208. The rongeur 200 can be sterilized by heat upon removal of the coil 210 and the battery pack 206. Alternatively, the device can be cold gas sterilized or irradiated.

The rod 212 can be adjustable along the longitudinal axis, either by threads or other means, so that it can be moved forward if necessary. Also, a safety mechanism for preventing activation of the switch 220, well known in electrically operated devices, can be included. This could consist of a mechanical interference between the trigger and the switch to prevent activation of the switch 220.

In use, the surgeon would insert the rongeur 200 around the lamina to be cut and the trigger 218 would be pulled. The pulling of the trigger would cause the slide drive member 20 and the cutting/storage member 50 to be driven forward to close against the foot plate 16 cutting the bone, and then automatically returned to the original open position. Releasing the trigger 214 would permit the cutting/storage element 50 to return to its open position. The surgeon would then move the rongeur 200, without removing the rongeur 200 from the wound, to a new area for biting the bone, again activating the trigger and causing the rongeur to close. The device could be programmed to close at a predetermined rate, so that it would automatically open and close. After completion of the cutting procedure the rongeur 200 would be removed and the cutting/storage member 50 removed and replaced in the same manner described above for the manual rongeur 10.

While the present invention has been described in association with the preferred embodiment, it is recognized that other variations of the present invention may be made without departing from the scope of the present invention.

What is claimed is:

1. A method for cutting bone or cartilage, the method comprising the steps of:
   providing a rongeur having a shaft with a mid-longitudinal axis, a foot plate extending from the shaft, and a storage member in moveable relationship to the shaft, the storage member having a cutting edge and a storage area adapted to store multiple cuts of bone or cartilage;
   positioning the rongeur at a site where the bane or cartilage is to be cut;
   cutting bone or cartilage with the rongeur to produce multiple cut pieces of bone or cartilage;
   storing the cut pieces of bone or cartilage spaced apart from the cutting edge in the storage area of the storage member;
   preventing the cut pieces of bone or cartilage from contacting the shaft from within the storage member; and
   moving the storage member away from the mid-longitudinal axis of the shaft in a direction generally radial to the mid-longitudinal axis while the cut pieces of bone or cartilage are still in the storage area.

2. The method of claim 1, further comprising the steps of replacing the storage member with a second storage member and engaging the second storage member with the shaft.

3. The method of claim 2, further comprising the step of locking the second storage member to the shaft.

4. The method of claim 1, further comprising the step of disposing the storage member.

5. The method of claim 1, wherein the storage area increases in cross sectional area from one end of the storage member to another end of the storage member.

6. The method of claim 1, wherein the step of cutting includes reciprocating the storage member relative to the shaft to cut the bone or cartilage.

7. The method of claim 1, wherein the step of cutting includes manually cutting the bone or cartilage.

8. The method of claim 1, wherein the step of cutting includes electrically operating the rongeur to cut the bone or cartilage.

9. The method of claim 1, wherein the storage member is insertable into a carrier member, the step of moving including moving the carrier member away from the mid-longitudinal axis of the shaft in a direction generally radial to the mid-longitudinal axis.

10. The method of claim 9, further comprising the step of removing the storage member from the carrier member.

11. The method of claim 10, further comprising the steps of inserting a second storage member into the carrier member and attaching the carrier member to a portion of the shaft of the rongeur.

12. The method of claim 1, further comprising the step of removing the cut pieces of bane or cartilage from the storage area of the storage member after removal of the storage member from the shaft.

13. The method of claim 12, further comprising the step of utilizing the cut pieces of bone or cartilage removed from the storage member in another medical procedure.

14. The method of claim 1, wherein the step of cutting includes producing multiple cut pieces of bone or cartilage without removing the rongeur from the patient.

15. The method of claim 1, further comprising the steps of moving the storage member toward the shaft from a direction above the shaft, and engaging the storage member to the shaft.

16. The method of claim 15, wherein the step of engaging includes snap fitting the storage member onto the shaft.

17. The method of claim 1, further comprising the step of replacing the cutting edge with a different cutting edge.

18. The method of claim 1, wherein the step of storing is performed without ejecting the pieces of bone or cartilage stored within the storage member while the rongeur is being used to take additional cuts of bone or cartilage.

19. The method of claim 1, further comprising the step of replacing the foot plate with a second foot plate.

20. The method of claim 1, further comprising the step of releasably locking the storage member to the rongeur.

* * * * *

UNITED STATES PATENT AND TRADEMARK OFFICE
CERTIFICATE OF CORRECTION

PATENT NO. : 7,297,147 B2  Page 1 of 1
APPLICATION NO. : 11/371387
DATED : November 20, 2007
INVENTOR(S) : Gary K. Michelson It is certified that error appears in the above-identified patent and that said Letters Patent is hereby corrected as shown below:

Title Page 2, Item (56) References Cited:
U.S. Patent Documents, line 5: change "Michaelson" to --Michelson--.

Column 12, line 37:
Change "bane" to --bone--.

Column 13, line 16:
Change "bane" to --bone--.

Signed and Sealed this

Fourth Day of March, 2008

JON W. DUDAS
*Director of the United States Patent and Trademark Office*